United States Patent [19]

Robbins

[11] 4,428,888

[45] Jan. 31, 1984

[54] METHOD FOR PREPARATION OF N-PHOSPHONOMETHYLGLYCINE

[75] Inventor: Jeffrey D. Robbins, Berkeley, Calif.

[73] Assignee: Stauffer Chemical Company, Westport, Conn.

[21] Appl. No.: 408,322

[22] Filed: Aug. 16, 1982

[51] Int. Cl.$^3$ .............................................. C07F 9/38
[52] U.S. Cl. ............................. 260/502.5 F; 560/155
[58] Field of Search .................. 260/502.5 F, 502.5 E

[56] References Cited

U.S. PATENT DOCUMENTS

| | | | |
|---|---|---|---|
| 2,847,442 | 8/1958 | Sallmann | 260/502.5 E |
| 3,288,846 | 11/1966 | Irani et al. | 260/502.5 F |
| 3,366,677 | 1/1968 | Quimby | 260/502.4 A |
| 3,547,728 | 12/1970 | Balde et al. | 260/502.5 E |
| 4,053,505 | 10/1977 | Dutra | 260/502.5 F |
| 4,235,809 | 11/1980 | Redmore | 546/21 |

Primary Examiner—J. E. Evans
Attorney, Agent, or Firm—Paul R. Martin

[57] ABSTRACT

Disclosed is a method for the preparation of N-phosphonomethylglycine which comprises the steps of (1) reacting 1,3,5-tris(alkoxy- or aryloxy-substituted carbonylmethyl) hexahydro-s-triazine, with a substituted phosphorus compound having the formula PXYZ wherein X is a halogen, Y and Z are independently selected from the group consisting of halogen, alkoxy having from 1 to 10 carbon atoms, and aryloxy, in the presence of a protic acid and a low molecular weight carboxylic acid; (2) heating said reactants to a temperature ranging from about 10° to about 25° C. for a sufficient period of time to cause the formation of an N-phosphonomethylglycine ester,; and (3) hydrolyzing said phosphonomethylglycine ester to N-phosphonomethylglycine.

6 Claims, No Drawings

METHOD FOR PREPARATION OF N-PHOSPHONOMETHYLGLYCINE

BACKGROUND OF THE INVENTION

This invention relates to a novel method for the preparation of N-phosphonomethylglycine, a compound which is a known herbicide and plant growth regulator.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and post-emergence herbicides. The pre-emergence herbicides are incorporated into the soil prior to the emergence of the weed plants from the soil, and the post-emergence herbicides are applied to plant surfaces after emergence of the weeds or other unwanted plants from the soil.

One of the earliest post-emergence herbicides used commercially was 2,4-D (2,4-dichlorophenoxyacetic acid). After a number of years of use of this and similar compounds such as 2,4,5-T (2,4,5-trichlorophenoxyacetic acid), it was found that certain decomposition products of these herbicides were long lasting and were not biodegradable. While there has been some dispute between governmental agencies and commercial interests regarding the effects of residual products of 2,4-D, 2,4,5-T and similar compounds, the agencies nevertheless restricted the use of these herbicides in the United States some years ago. Since that time, efforts have been made to develop herbicides which are biodegradable into harmless residues within a relatively short time after their application.

One such compound, which has been found to be biodegradable, yet which is effective as a herbicide and plant growth regulator when employed at lower rates, is N-phosphonomethylglycine and various salts thereof. The N-phosphonomethylglycine and agriculturally effective salts have been approved for use by the U.S. Government, and, as a consequence, this herbicide has become extremely successful commercially.

The N-phosphonomethylglycine and certain salts are the only effective and approved post-emergence herbicides in the field. The present commercial compound is the isopropylamine salt of N-phosphonomethylglycine and derivatives thereof.

In field use it is normally applied in amounts of from 0.01 to about 20 pounds per acre, preferably from 2 to 6 pounds per acre.

The N-phosphonomethylglycines, and certain soluble salts thereof, can be made in a number of different ways. One such method, as described in U.S. Pat. No. 3,160,632 (Toy et al., Dec. 8, 1964) is to react N-phosphinomethylglycine (glycinemethylenephosphinic acid) with mercuric chloride in a water solvent at reflux temperature, and subsequently separating the reaction products. Another method is the reaction of ethyl glycinate with formaldehyde and diethylphosphite. The latter method is described in U.S. Pat. No. 3,799,758 (Franz, Mar. 26, 1974). In addition, there is a whole series of patents, relating to N-phosphonomethylglycines, their salts, and derivatives thereof, described as being useful herbicides and plant growth regulators. Such additional patents relating to the N-phosphonomethylglycines, methods of application, methods of preparation, salts, and derivatives, include U.S. Pat. No. 3,868,407, U.S. Pat. No. 4,197,254, and U.S. Pat. No. 4,199,354, among others.

Because of the importance of N-phosphonomethylglycine and certain salts as a herbicide, other methods of making the compounds are constantly being sought in order to provide improved or alternate methods of manufacture.

SUMMARY OF THE INVENTION

It has now been discovered that N-phosphonomethylglycine can be produced by:

(1) reacting 1,3,5-tris(alkoxy- or aryloxycarbonylmethyl) hexahydro-s-triazine with a substituted phosphorus compound having the formula PXYZ wherein X is a halogen, Y and Z are each independently selected from the group consisting of halogen, alkoxy having from 1 to 10 carbon atoms and aryloxy, in the presence of a relatively strong protic acid and a low molecular weight carboxylic acid having from 1 to 6 carbon atoms, and (2) hydrolyzing the intermediate ester of N-phosphonomethylglycine thus formed to convert said ester of N-phosphonomethylglycine to N-phosphonomethylglycine.

Preferred starting compounds for use in the method of the invention include 1,3,5-tris(ethoxycarbonylmethyl) hexahydro-s-triazine, and 1,3,5-tris(propoxycarbonylmethyl) hexahydro-s-triazine. Other suitable compounds would include the aryloxy substituted carbonylmethyl hexahydro-s-triazines.

Preferred substituted phosphorus compounds for use in the above process include phosphorus trichloride, phosphorus tribromide, ethyl dichlorophosphite, and diethyl chlorophosphite.

Preferred relatively strong protic acids for use in the above process include hydrochloric acid, hydrobromic acid, hydriodic acid, sulfuric acid, and phosphoric acid, with the most preferred acid being hydrochloric acid.

Suitable low molecular weight carboxylic acids include acetic acid, propanoic acid and butanoic acid.

When phosphorus trichloride is the trivalent phosphorus compound used, the reaction products for the first step of the process are N-phosphonomethylglycine, C-ethyl ester hydrochloride, and a carboxylic acid chloride. N-Phosphonomethylglycine can then be produced by hydrolyzing the intermediate ester with a suitable hydrolyzing agent to yield N-phosphonomethylglycine.

An optional feature of the method of the invention is that the N-phosphonomethylglycine compound produced as indicated above, can then be reacted with a suitable base to produce the soluble salts of the acid. Suitable bases for this purpose would include sodium hydroxide, potassium hydroxide, trimethylsulfonium hydroxide or the hydroxide or oxide of any agriculturally acceptable cation.

In the process of the invention, phosphorus trichloride, hydrogen chloride, and acetic acid, are preferably used to react with the starting compound 1,3,5-tris(alkoxy- or aryloxycarbonylmethyl) hexahydro-s-triazine. Alternatives to these compounds can be used, however. In the case of phosphorus trichloride, alternative compounds would be, for example, phosphorus tribromide, phosphorus dibromochloride, and ethyl dichlorophosphite. Instead of hydrogen chloride, suitable alternatives would be hydrogen bromide, hydriodic acid, sulfuric acid, and phosphoric acid. Instead of acetic acid, any low molecular weight carboxylic acid would be suitable, including propanoic and butanoic acid.

The product of the above described reaction, the N-phosphonomethylglycine ester, is then hydrolyzed in aqueous acid, with subsequent alkaline work-up, or in aqueous base with subsequent acidic work-up to afford N-phosphonomethylglycine.

The overall process, using the preferred ingredients, can be represented as follows:

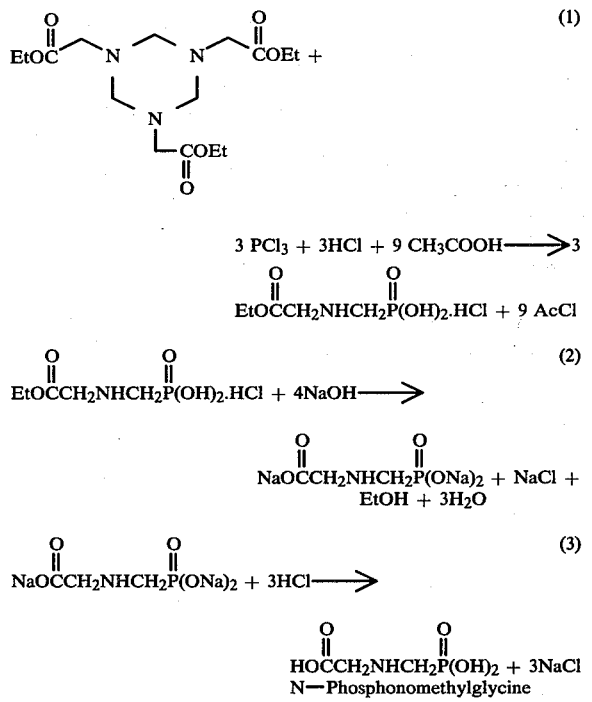

The hexahydro-s-triazine and phosphorus trichloride are used in approximately stoichoimetric amounts and the hydrochloric acid and acetic acid in excess. The reaction is conducted at a temperature ranging from about 0° to about 50° C., preferably 10° to 25° C., at atmospheric pressure, and for a time sufficient to bring the reaction to completion, which preferably ranges from about 3 to about 18 hours.

This invention will be better understood by reference to the specific example which follows, which serves to illustrate the instant invention.

EXAMPLE 1

Preparation of N-Phosphonomethylglycine, Trisodium Salt

To a three-necked, 50 milliliter (ml) round-bottom flask equipped with a magnetic stirrer, a nitrogen bubbler, a reflux condenser, and a thermometer, and a heating mantle was added 10 ml (175 mmole) of acetic acid, under a nitrogen atmosphere. Thereafter, 2.6 ml (30 mmole) of phosphorus trichloride was added in one portion to the flask. The solution was cooled in an ice bath and thereafter 2 grams (g) (54 mmole) of hydrochloric acid was added slowly. At the same time, 3.45 g (10 mmole) of 1,3,5-tris(ethoxycarbonylmethyl)hexahydro-s-triazine was dissolved in 40 ml of acetic acid and placed in a dropping funnel. The hexahydro-s-triazine solution was then added over 0.9 hours at 6°-12° C. Hydrogen chloride addition was continued during the addition of the hexahydro-s-triazine and then stopped. A total of 6.5 g (178 mmole) of hydrogen chloride was added. The reaction mixture was stirred for ca. one hour at 10°-15° C. and then for ca. 18 hours at 20° C. Thereafter, 5.0 ml of water was added dropwise at approximately 20° C. over a 20 minute period to give a cloudy colorless solution. This solution was stirred at ambient temperature for 2.5 hours, and concentrated in vacuo at 40° C., yielding an opaque colorless oil. This oil (4.8 g) was then taken up in 5.0 ml of water, and basified to a pH of 12 with 10 molar sodium hydroxide. Then 5.0 ml more of 10 molar sodium hydroxide was added. Thereafter the solution was heated to reflux and maintained at reflux for a period of approximately 6 hours. The reaction mixture was analyzed by $^{13}C$ nuclear magnetic resonsance (nmr) spectroscopy and by high performance liquid chromatography (hplc) and found to contain the trisodium salt of N-phosphonomethylglycine in 41% yield.

It will be recognized by those skilled in the art that variations in the quantities of reactants, temperatures used, mole ratios used, and time of reaction can be made in the method of the invention without departing from the spirit and scope of the appended claims.

What is claimed is:

1. A method for the preparation of N-phosphonomethylglycine which comprises the steps of
    (1) reacting 1,3,5-tris(alkoxy- or aryloxy-substituted carbonylmethyl) hexahydro-s-triazine, with a substituted phosphorus compound having the formula PXYZ wherein X is a halogen, Y and Z are independently selected from the group consisting of halogen, alkoxy having from 1 to 10 carbon atoms, and aryloxy, in the presence of a relatively strong protic acid and a low molecular weight carboxylic acid,
    (2) heating said reactants to a temperature ranging from about 10° to about 25° C. for a sufficient period of time to cause the formation of an N-phosphonomethylglycine ester, and
    (3) hydrolyzing said N-phosphonomethylglycine ester to N-phosphonomethylglycine.

2. The method of claim 1 in which said substituted phosphorus compound is selected from the group consisting of phosphorus trichloride, phosphorus tribromide, ethyl dichlorophosphite and diethyl chlorophosphite.

3. The method of claim 1 in which said low molecular weight carboxylic acid is selected from the group consisting of acetic, propanoic and butanoic acid.

4. The method of claim 1 in which said 1,3,5-tris(alkoxy- or aryloxy-substituted carbonylmethyl) hexahydro-s-triazine and substituted phosphorus compound of the formula PXYZ are used in approximately stoichiometric amounts and said carboxylic acid and relatively strong protic acid are used in excess.

5. The method of claim 1 in which said hexahydro-s-triazine is 1,3,5-tris(ethoxycarbonylmethyl) hexahydro-s-triazine.

6. The method of claim 1 in which said hexahydro-s-triazine is 1,3,5-tris(propoxycarbonylmethyl) hexahydro-s-triazine.

* * * * *